United States Patent [19]

Kaufhold et al.

[11] Patent Number: 5,527,969
[45] Date of Patent: Jun. 18, 1996

[54] PROCESS FOR PREPARING ACETALDEHYDE DIETHYL ACETAL

[75] Inventors: Manfred Kaufhold, Marl; Moustafa El-Chahawi, Troisdorf, both of Germany

[73] Assignee: Huels Aktiengesellschaft, Marl, Germany

[21] Appl. No.: 384,871

[22] Filed: Feb. 7, 1995

[30] Foreign Application Priority Data

Feb. 12, 1994 [DE] Germany .................. 44 04 515.8

[51] Int. Cl.$^6$ .................. C07C 41/56; C07C 43/303
[52] U.S. Cl. .................. 568/605; 568/594
[58] Field of Search .................. 568/605, 594

[56] References Cited

U.S. PATENT DOCUMENTS 2,519,540  8/1950  Bramwyche et al. .................. 568/605
2,535,458  12/1950  Robeson .................. 568/605

FOREIGN PATENT DOCUMENTS 147461   8/1994   Australia .................. 568/594
512501   11/1992  European Pat. Off. .................. 568/594
9417024  7/8199   WIPO .................. 568/594

*Primary Examiner*—Joseph E. Evans
*Attorney, Agent, or Firm*—Oblon, Spivak, McClelland, Maier & Neustadt

[57] ABSTRACT

A process for preparing acetaldehyde diethyl acetal is provided which involves:

reacting acetaldehyde with ethanol in the presence of an acid catalyst and in the presence of an entrainer having a boiling point of from 25° to 75° C.

8 Claims, No Drawings

PROCESS FOR PREPARING ACETALDEHYDE DIETHYL ACETAL

BACKGROUND OF THE INVENTION

1. Field of the invention

The present invention relates to an industrial process for preparing acetaldehyde diethyl acetal (herein called acetal) by reaction of acetaldehyde with ethanol in the presence of an acid catalyst, and in the presence of an entrainer having a boiling point of from 25° to 75° C.

2. Description of the Related Art

The preparation of acetal is known in the literature. The process described in Org. Synth. Coll. Vol. I, 1948, page 1, is a laboratory process which, because of its high consumption of chemicals and the associated costs, is out of the question for industrial implementation.

For higher-boiling aldehydes and ketones such as butyraldehyde, industrially useful catalytic acetalization processes are known in the literature, (see Weygand/Hilgetag, Org.-Chem., Experimentierkunst (1970), J. A. Barth-Verlag Leipzig, page 393). The acetalization process is an equilibrium process which follows the general scheme below:

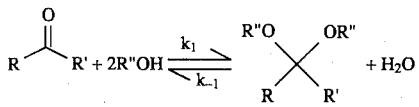

In the acetalization of higher aldehydes and ketones, the water of reaction formed is removed by means of an entrainer which boils at a lower temperature than the aldehyde or the ketone, or by means of the sparingly water-soluble aldehyde or ketone itself. This removal of the water of reaction shifts the equilibrium of the reaction to the desired side providing more complete reactions, (i.e. $k_1 >> k_{-1}$). Using the catalytic reaction, these are the only known means for achieving high yields.

Unfortunately, this conventional mode of operation is not possible in the case of low-boiling acetaldehyde (bp. 20.2° C.), since the starting material tends to distill out of the reactor and escapes reaction (i.e. removal of acetaldehyde makes the equilibrium shift such that $k_{-1} >> k_1$). Acetaldehyde is also not suitable for removal of water, because it is miscible with water in any ratio. The conventional acetalization methods are thus basically not applicable to acetaldehyde.

DE-A-34 03 426 proposes an industrial acetalization process which uses solid acid catalysts and in which the workup of the reaction product is carried out by the addition of large amounts of water and large amounts of an extractant immiscible with water. The extractant takes up the acetal and the unreacted aldehyde. The water takes up the alcohol. This separation is very important here, because in the case of acetal this forms an azeotrope with ethanol (boiling point: 78° C., acetal content: 24%), so that a distillation alone would not give a pure product.

However, this process has the disadvantage that it requires large amounts of water and extractant, the handling of which leads to uneconomically high costs. In addition, in this and in all other known acetalization processes, one only obtains, at best, the equilibrium state in the reaction between aldehyde and alcohol, i.e., a large part of the aldehyde always remains unreacted and has to be recovered or destroyed, thus incurring additional costs.

It is therefore desirable to have a simple process which allows the reaction of acetaldehyde beyond the equilibrium state and which uses an effective workup which does not require large amounts of auxiliaries. Furthermore, there is great interest in a process for reacting acetaldehyde with ethanol in the presence of a catalyst and simultaneously removing the water of reaction to achieve a high acetaldehyde conversion with little technical effort and without the use of expensive chemicals.

SUMMARY OF THE INVENTION

Accordingly, it is one object of the present invention to provide an economical process which is capable of providing acetal by reaction of acetaldehyde with ethanol.

A further object of the present invention is to provide a process for preparation of acetal which allows the reaction of acetaldehyde and ethanol beyond the equilibrium state and improves the efficiency of use of the acetaldehyde raw material.

A further object of the present invention is to provide a process for preparation of acetal which uses an effective and efficient workup procedure after the acetalization reaction, to recover the acetal formed without the use of large amounts of auxiliaries and extractants.

These objects and others have been satisfied by the discovery of a process for the preparation of acetal comprising reacting acetaldehyde and ethanol in the presence of an acid catalyst and further in the presence of an entrainer having a boiling point of from 25° to 75° C. Preferably, the reaction is carried out in the presence of an entrainer at its boiling point.

DETAILED DESCRIPTION OF THE PREFERRED EMBODIMENTS

The present invention relates to a process for preparing acetaldehyde diethyl acetal, comprising:

reacting acetaldehyde with ethanol in the presence of an acid catalyst and in the presence of an entrainer having a boiling point of from 25° to 75° C.

Acetaldehyde diethyl acetal (acetal) is an important fragrance and a raw material for fragrances and pharmaceutical products. Elimination of alcohol from acetal easily gives, for example, vinyl ethyl ether which in turn is a reactive building block for pharmaceutical and fragrance syntheses.

Suitable entrainers for use in the present process include customary water-insoluble solvents such as hydrocarbons, chlorinated hydrocarbons and ethers. The primary requirements for the entrainer are that it must be essentially water-insoluble (<3% soluble in water) and the boiling point has to be significantly higher than that of acetaldehyde (20.8° C.) and lower than that of ethanol (78.5° C.). Preferably, the boiling point is in the range from 40° to 70° C. Examples of suitable entrainers are pentane, hexane, industrial hydrocarbon mixtures, methylene chloride and diethylether. For economic reasons, use is preferably made of low-cost petroleum fractions having the appropriate boiling range, with hexane (boiling point about 69° C.) being very particularly preferred.

The amount of entrainer used in the present process is generally from 10 to 500 g, preferably from 20 to 100 g, per mol of aldehyde.

The molar ratio of acetaldehyde to ethanol must be at least 1:2 and is usually from 1:2 to 1:20, preferably from 1:2.2 to 1:8 and most preferably from 1:2.5 to 1:3.5.

Suitable acidic catalysts for use in the present process includes the conventional known acid catalysts, such as mineral acids and carboxylic acids. For economic reasons, phosphoric acid and sulphuric acid are preferred. The amount of catalyst is very small in the present acetalization reactions, ranging from 0.01 to 0.1 g per mol of aldehyde, preferably from 0.02 to 0.08 g per mol of aldehyde.

The process of the present invention is preferably carried out in an apparatus for removing water from the system such as a conventional Dean-Stark apparatus. While the order of addition of reactants is not critical to the success of the reaction, in a preferred embodiment the entrainer is first placed in the reactor (reaction flask) and heated to boiling. Acetaldehyde and ethanol are then added to form a reaction mixture. A distillate mixture comprising over 50% of ethanol and water is distilled out during reaction, with unreacted acetaldehyde present in the distillate mixture being recovered by a further distillation and being recycled to the reaction mixture. The acetal formed is obtained from the bottom product of the reactor.

The addition of aldehyde and ethanol is preferably carried out by first adding a first portion of ethanol to the reaction vessel along with the entrainer and heating the mixture to boiling. Acetaldehyde and a second portion of ethanol, separately or in admixture, are then metered in. In this embodiment it is preferred that the first portion of ethanol be an amount of from 5 to 20% by weight of the total amount of the first and second portions of ethanol.

The distillate from the reactor is condensed and separated into 2 phases by means of a water separator. While the non-polar entrainer phase is directly recirculated, the polar phase containing predominantly ethanol and water is separated off. The acetaldehyde still present in the polar phase is then separated off and recovered by distillation or boiling under reflux (boiling out). The acetaldehyde vaporized in that distillation can be condensed in a dry ice condenser.

In the apparatus for removing water from the system, the temperature of the water separator and that of the condenser above the water separator is preferably set to above 20° C. As a result, part of the acetaldehyde remains in gaseous form. This gaseous acetaldehyde can be condensed at a later point and recirculated to the reactor. At the same time, this results in the acetaldehyde content of the entrainer phase being below 50%, preferably below 20%.

Surprisingly, high conversions of acetaldehyde are obtained in the acetalization of the acetaldehyde with ethanol in the presence of the customary acid catalysts even at relatively high temperature, at the boiling point of a suitable entrainer. This is achieved by distilling out of the system a water/alcohol mixture which can be separated from the entrainer, and ensuring that the aldehyde content of the phases which separate is not too high and that the aldehyde distilling off is condensed out and recirculated to the reactor. However, in order to maximize the absolute yield of acetal and minimize the amount of acetaldehyde used, care should be taken to ensure that the amount of acetaldehyde which distills off and no longer reacts is not too high in comparison with the amount of aldehyde which reacts to give the acetal.

A great advantage of this process is that it can be easily regulated and that it is possible to monitor exactly the amounts of aldehyde which are reacted and condensed out by the use of techniques such as conventional quantitative gas chromatography or liquid chromatography. This makes the process particularly well-suited to industrial implementation. It requires no special apparatus other than the capability of removing water during reaction. The most important aspect is to adhere to the temperatures specified above so that the aldehyde behaves in the desired manner. In addition, it is advantageous that the acetal does not distill over in significant amounts in the form of an azeotrope with the entrainer, ethanol and water and therefore essentially remains in the bottom of the reactor. This favorable behavior of the specific mixture of materials and also the suitable reaction rates and the rapid phase separation could not have been foreseen and are surprising. Additionally, the process enjoys the advantages of simple operation and good economics.

The process of the present invention can be carried out, for example, in an apparatus which essentially consists of a stirred reactor fitted with a dropping funnel, a water separator having a reflux condenser fitted on top and a distillation flask, with reflux condenser, connected to the water separator, and appropriate cross-connections to ensure that the acetaldehyde condensed in the condensers can be recirculated into the dropping funnel or directly into the stirred reactor. Preferably the dropping funnel is coolable to a temperature of from −5° to −10° C., to provide efficient handling of an ethanol/acetaldehyde mixture.

In an embodiment, the entrainer is heated to boiling in the reactor, preferably together with a part of the ethanol, whereupon a mixture of acetaldehyde and the remaining ethanol is added. Two phases are formed in the water separator, of which the entrainer phase is recirculated into the reactor and the aqueous phase is drained into the distillation flask where it is heated to boiling under reflux, with acetaldehyde being vaporized, condensed and collected. After the addition of fresh aldehyde is complete, the aldehyde condensed out is added dropwise. The process can also be modified and, for example, the aldehyde which has condensed out again used in a single change in the next batch rather than added dropwise.

Having generally described this invention, a further understanding can be obtained by reference to certain specific examples which are provided herein for purposes of illustration only and are not intended to be limiting unless otherwise specified.

EXAMPLE

The reactor of an apparatus as described above was initially charged with:

300 g (6.43 mol) of ethanol (98.7% pure)

300 g of n-hexane as entrainer 0.37 g of concentrated sulphuric acid

In the course of 7.5 hours, the following solution was added, first at room temperature, then after 1 hour at from 54 to 52° C. while boiling under reflux:

353 g (8.0 mol) of acetaldehyde 598 g (12.8 mol) of ethanol (98.7% pure)

Over a period of 30 minutes, from 21 to 30 ml of aqueous phase were obtained, and were drained into the distillation flask.

Excess acetaldehyde was condensed out and collected. At the end of the dropwise addition, about 120 ml had been collected. After a further reaction time of 5 hours the acetaldehyde collected was added dropwise to the reaction mixture over a period of 2 hours.

The aqueous phase was continuously separated off and drained, while the entrainer phase was recirculated to the reaction mixture.

After 20 hours, the amount distilled per half hour was about 15 ml; after 24 hours, about 12 ml; after 26 hours, 8 ml; and after 29 hours, only 3 ml, i.e., the reaction slowed down increasingly towards the end.

The gas-chromatographic analyses in the following tables show the exact course of the reaction. The time of dropwise addition is here not included in the specified reaction time (RT).

TABLE 1

Reaction mixture in the reactor

| RT in h | Aldehyde | Ethanol | Acetal | Water | Hexane |
|---|---|---|---|---|---|
| 15 | 8.0 | 11.5 | 55.0 | 1.1 | 22.6 |
| 22 | 4.6 | 12.9* | 61.3 | 0.8 | 18.7 |
| 29 | 3.0 | 8.1 | 62.3 | 0.2 | 25.0 |

*After 17 hours, 160 g of ethanol and 0.2 ml of conc. sulphuric acid were added over a period of 1 hour.

TABLE 2

Contents of distillation flask

| RT in h | Aldehyde | Ethanol | Acetal | Water | Hexane |
|---|---|---|---|---|---|
| 15 | 7.9 | 62.1 | 0.8 | 21.8 | 7.4 |
| 22 | 5.4 | 64.6 | 1.5 | 22.2 | 6.2 |
| 29 | 5.3 | 63.2 | 2.0 | 22.0 | 7.4 |

TABLE 3

Entrainer phase in the separator

| RT in h | Aldehyde | Ethanol | Acetal | Water | Hexane |
|---|---|---|---|---|---|
| 15 | 10.4 | 11.0 | 0.4 | 1.1 | 76.6 |
| 22 | 6.7 | 10.1 | 2.0 | 0.9 | 80.0 |
| 29 | 7.8 | 11.5 | 0.3 | 1.1 | 78.5 |

TABLE 4

Water phase in the separator

| RT in h | Aldehyde | Ethanol | Acetal | Water | Hexane |
|---|---|---|---|---|---|
| 22 | 23.0 | 49.0 | 1.6 | 10.9 | 38.0 |
| 29 | 21.6 | 46.5 | 0.5 | 10.8 | 20.0 |

After 29 hours, the reaction mixture was made alkaline with 2.46 g of 50% strength sodium hydroxide solution to reach a pH of 10.0.

The azeotrope distillation was then continued for about 2 hours to separate the ethanol from the n-hexane. Then, since there was no longer any phase separation, from about 10 to 20 ml/h of water were added to the distillate, and 128 g ethanol was recovered over a 4 hour period.

The ethanol separated out had the following composition:

| Ethanol | 47.1% |
|---|---|
| Water | 50.4% |
| Acetal | 0.7% |
| Aldehyde | 1.1% |
| Hexane | 0.5% |

The bottom product, 991 g, had the following composition:

| Acetal | 71.2% |
|---|---|
| Hexane | 27.3% |
| Water | 0.1% |

Purification of the bottom product, 985 g, by distillation at atmospheric pressure gave the fractions shown in Table 5.

TABLE 5

| Fraction No. | Boiling Range °C. | Weight in g | Content in % | | | |
|---|---|---|---|---|---|---|
| | | | Hexane | Acetal | Ethanol | Water |
| 1 | 66–70 | 230 | 96.5 | 2.7 | 0.2 | 0.3 |
| 2 | 73–102 | 45 | 36.2 | 59.9 | 1.6 | 0.8 |
| 3 | 103 | 675 | | 99.1 | 0.3 | 0.1 |
| Residue | | 32 | | | | |
| Cold trap | | 2 | | | | |
| Total | | 984 | | | | |

The yield of acetal was 74% of theory, based on aldehyde used. The conversion of aldehyde was 80%, after acetalization and prior to the neutralization. Based on aldehyde converted, the yield was 92%.

What is claimed as new and is desired to be secured by Letters Patent of the United States is:

1. A process for preparing acetaldehyde diethyl acetal, comprising:

heating an entrainer and a first portion of ethanol to boiling;

adding acetaldehyde, a second portion of ethanol and a catalyst to form a reaction mixture;

distilling from said reaction mixture a distillate mixture comprising over 50% of ethanol and water;

recovering unreacted acetaldehyde from said distillate mixture, and recycling said recovered unreacted acetaldehyde to said reaction mixture; and recovering acetaldehyde diethyl acetal from said reaction mixture.

2. The process according to claim 1, wherein said reacting step is carried out at a temperature at which said entrainer boils.

3. The process according to claim 1, wherein said entrainer has a boiling point of from 40° to 70° C.

4. The process according to claim 1, wherein ethanol is used in an amount of from 2 to 20 mol per mol of acetaldehyde.

5. The process according to claim 1, wherein ethanol is used in an amount of from 2.2 to 8 mol per mol of acetaldehyde.

6. The process according to claim 1, wherein said first portion of ethanol is from 5 to 20% by weight of a total of said first and second portions of ethanol.

7. The process according to claim 1, wherein said catalyst is a mineral acid or carboxylic acid catalyst.

8. The process of claim 1, wherein said entrainer is essentially water-insoluble and the boiling point thereof is significantly higher than that of acetaldehyde (20.8° C).

\* \* \* \* \*